(12) United States Patent  
Baca

(10) Patent No.: US 6,740,244 B2
(45) Date of Patent: May 25, 2004

(54) NEAR POINT OF USE LASER WATER TREATMENT SYSTEMS AND METHODS

(75) Inventor: Anthony Michael Baca, Albuquerque, NM (US)

(73) Assignee: Saltech Corporation, Albuquerque, NM (US)

( * ) Notice: Subject to any disclaimer, the term of this patent is extended or adjusted under 35 U.S.C. 154(b) by 92 days.

(21) Appl. No.: 10/029,444

(22) Filed: Dec. 21, 2001

(65) Prior Publication Data

US 2002/0079271 A1 Jun. 27, 2002

Related U.S. Application Data

(60) Provisional application No. 60/257,430, filed on Dec. 22, 2000.

(51) Int. Cl.[7] .................................................. C02F 1/30
(52) U.S. Cl. ........................... 210/748; 422/22; 422/186
(58) Field of Search ............................ 210/748; 422/22, 422/186

(56) References Cited

U.S. PATENT DOCUMENTS

| 4,661,264 | A | * | 4/1987 | Goudy, Jr. |
| 5,376,281 | A | * | 12/1994 | Safta |
| 5,480,562 | A | * | 1/1996 | Lemelson |
| 5,925,257 | A | * | 7/1999 | Albelda et al. |
| 6,464,868 | B1 | * | 10/2002 | Korin |
| 6,468,433 | B1 | * | 10/2002 | Tribelski |
| 6,482,370 | B2 | * | 11/2002 | Holsclaw et al. |

* cited by examiner

Primary Examiner—Betsey Morrison Hoey
(74) Attorney, Agent, or Firm—Luis Ortiz

(57) ABSTRACT

Water treatment methods and systems using laser light. Water enters a treatment area from waterline tubing wherein water within the treatment area is subjected to light from a laser as it passes through the treatment area, and wherein microorganisms contained within said water are reactive to the light and are killed. The water is provided to a point of use after treatment by light. The treatment area may be a junction box having an entry point for receiving water from input tubing connected to the input portion of the junction box; a fiber optic line or laser source coupled to the junction box for delivery of light from a laser into the junction box; and an exit point and/or port for providing water passing through the junction box to a point of use.

20 Claims, 2 Drawing Sheets

NEAR POINT OF USE LASER WATER TREATMENT SYSTEMS AND METHODS

This application claim priority to a Provisional Patent Application, Serial No. 60/257,430, filed Dec. 22, 2000, entitled "NEAR POINT OF USE LASER WATER TREATMENT."

FIELD OF THE INVENTION

The present invention is generally related to water treatment systems and methods and, more particularly, to the treatment of water near its point of use using laser technology.

BACKGROUND OF THE INVENTION

The microbiologic quality of water used in dental treatment must be improved. The medical profession, and in particular the dental industry and the medical research community, are taking steps to improve the quality of water used in patient care. Dental unit waterlines (the tubes that connect the high-speed handpiece, air/water syringe and ultrasonic scaler to the water supply) have been shown to harbor a wide variety of microorganisms including bacteria, fungi, and protozoans. These microorganisms colonize and replicate on the interior surfaces of the waterline tubing, inevitably resulting in adherent heterogeneous microbial accumulations termed "biofilms." Biofilms, once formed, serve as a reservoir significantly amplifying the numbers of free-floating microorganisms in water exiting the waterlines.

Dental unit water systems currently designed for general dental practice are incapable of efficiently and/or effectively delivering water of an optimal microbiologic quality. The ADA (American Dental Association) Council on Scientific Affairs has recommended (as adopted by the American Dental Association Board of Trustees, Dec. 13, 1995) that "an ambitious and aggressive course to encourage industry and the research community to improve the design of dental equipment so that by the year 2000, water delivered to patients during nonsurgical dental procedures consistently contains no more than 200 colony forming units per milliliter (cfu/ml) of aerobic mesophilic heterotrophic bacteria at any point in time in the unfiltered output of the dental unit; this is equivalent to an existing quality assurance standard for dialysate fluid that ensures the fluid delivery systems in hemodialysis units have not been colonized by indigenous waterborne organisms."

An illustration provided by Clinical Research Associates (CRA) in its March 1997 newsletter best illustrates the problem with respect to waterline contamination. Referring to FIG. 1, water may arrive at a building relatively microbe-free, at about 2 cfu/ml, because of the large diameter water delivery piping A. As water lines narrow within the building B (within inches in diameter) the microbe count increases to about 10 cfu/ml. At the junction box D within the dental unit (with tubing rated at less than an inch in diameter) the count is about 10,000 cfu/ml. After water has traveled about 10 feet within the dental station to the control center E, the count can go up to about 400,000 cfu/ml. Finally, at the sterile handpiece F and non-sterile air/water supply G (the sources of water into a patient's mouth) the microbe count entering the patients mouth can be 100,000 to 200,000 cfu/ml.

At the present time, commercially available options for improving dental unit water quality are limited and will involve some additional expense. They include: point-of-use filters; independent water reservoirs; chemical treatment regimens; dissassembly and sterilization, and daily draining and air purging regimens.

Dental unit water line filters may physically stop some bacteria from progressing through dental units, but the effectiveness of their use has not seen much research to clearly demonstrates their effectiveness, and microorganisms are capable of developing within the waterline or apparatus that exists after the filter's location. Furthermore, overuse or failure of a filter can lead to even higher levels of microorganisms.

Separate water systems allow dentists to disconnect their dental unit from the municipal water supply and replace it with a sterile water bottle. Such systems are most advantages to practitioners who are remodeling or opening up a new office due to the extensive plumbing requirements; however, microorganism growth within the resident system cannot be prevented.

Chemical approaches to disinfecting dental unit water lines have enjoyed varying success. One approach is the use of iodine to disinfect waterlines. The safety and efficacy of chemical disinfection protocols have not been sufficiently validated in the past; therefore the Council has strongly discouraged dentists from treating their dental unit waterlines chemically. In particular, the Council has warned against the use of glutaraldehyde in treatment-water delivery systems to meet the goals set out in the ADA's Statement on Dental Unit Waterlines. Glutaraldehyde is a recognized health hazard; it is a known dermal, mucosal, respiratory and systemic irritant that, as stated on its labeling, is only intended for use in closed containers. In addition to the potentially serious adverse health effects that may be associated with glutaraldehyde when used in dental unit waterlines, such use will essentially fix or "glue" the biofilm matrix to the surface of the waterline, leaving an ideal environment for microbial re-colonization.

Entire dental unit waterline sterilization is another technique being investigated. Such methods would require the dissasembly and sterilization of components within the dental station (in particularly the water delivery portions) that can be heat sterilized. Although such a system should be convenient for dentists because of their use of heat sterilization on handpieces and other equipment, such methods would require much added labor for dental office staff to effectively disassemble, sterilize, and reassemble waterlines.

Draining and air purging regimes, although the simplest method to employ, does not directly target the elimination of biofilm within system tubing.

Some combination of the above strategies may be necessary to control, biofilm formation and to achieve the desired level of water quality. To date, however, there is insufficient data to establish the effectiveness of available methods. Many of the described methods do not directly address microorganism buildup that may occur within waterlines throughout the day. Furthermore, many of the described methods may not be cost effective for the industry. Therefore a wider range of alternatives and adjuncts to the above listed options is desirable. It is further desirable that treatment in waterlines occur at a point closest to the "point of use" in order to ensure a higher probability of water treatment system effectiveness.

SUMMARY OF THE INVENTION

The present invention addresses the need for more effective and cost efficient water treatment. The present invention provides for the laser treatment of water near its point of use within a waterline and/or at a waters source.

As described in an embodiment of the invention, water enters a treatment area, such as a junction box, from waterline tubing wherein it is subjected to light from laser light as it passes through a treatment area, wherein microorganisms contained within said water are reactive to the light and are killed. The water is then provided to a point of use.

In another embodiment of the invention, the treatment area may be a junction box having an entry point for receiving water from input tubing connected to the input portion of the junction box. A fiber optic line and/or laser source can be optically coupled to the junction box for delivery of light treatment into the junction box. An exit point then provides water passing through the junction box to a point of use.

In another embodiment of the invention, the junction box is integrated within and provided near the distal end (head) of a dental handpiece. Input waterline tubing carries water from the control panel of a dental system to the handpiece where the tubing is connected to an input portion of the junction box. Fiber optic cabling and/or a laser can be optically coupled to the junction box for delivery of light treatment into the junction box. The tubing and/or passageway within the head of the handpiece can be connected to the output portion of the junction box. An exit port within the head can then, provide water to its intended point of use.

In yet another embodiment of the invention, the head can be removably connected to the handpiece and/or junction box.

Another embodiment of the invention can provide a beam directing mechanism, such as a splitter or switching mechanism, for directing light between an exit port in the dental instrument and/or the water treatment area or junction box within the hand piece and a treatment area at a point of use (e.g., a dental patients mouth).

DESCRIPTION OF THE DRAWINGS

The summarized and other features, aspects and advantages of the present invention will become better understood with regard to the following description, appended claims and accompanying drawings where:

DETAILED DESCRIPTION OF THE PREFERRED EMBODIMENTS

Figure 1:
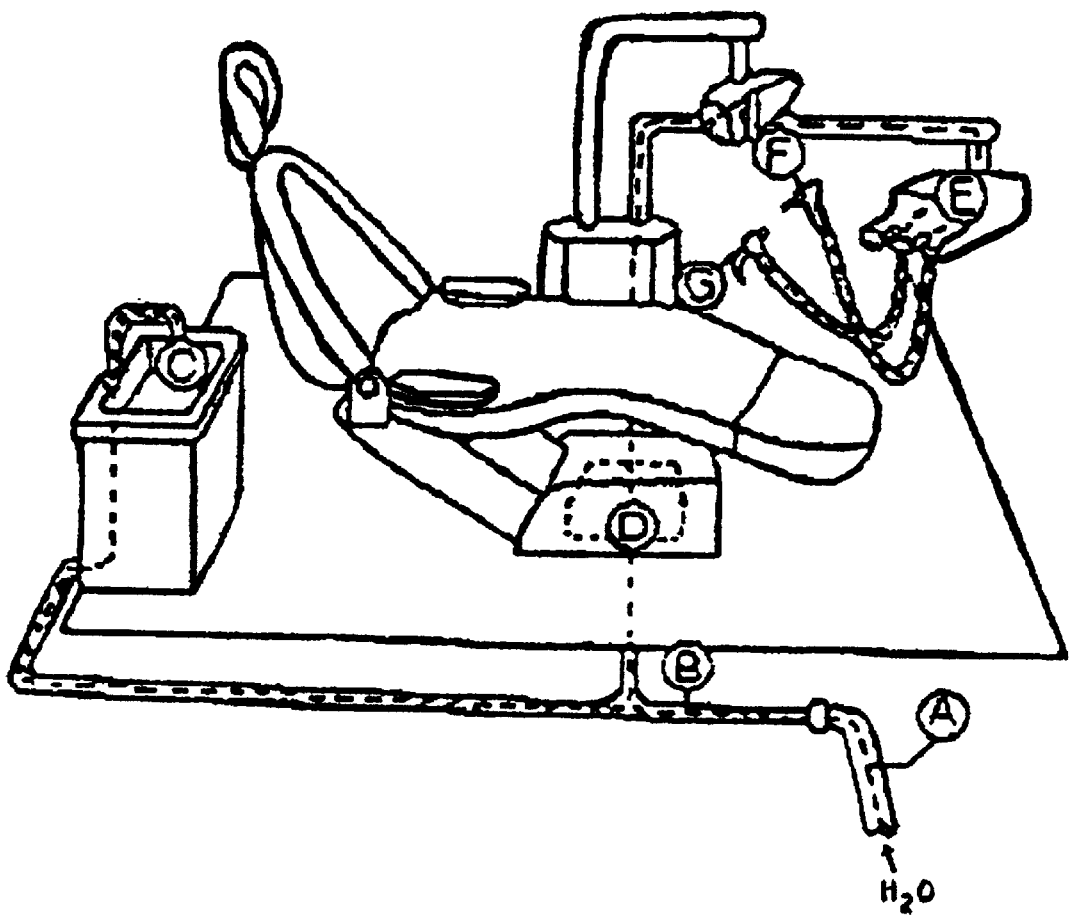
FIG. 1 illustrates a prior art dental system having a water delivery system with items A–G.

The use of lasers in medical handpieces is not new. For examples of medical laser use see: U.S. Pat. No. 5,851,112 to Daikuzono et al., "Dental Handpiece"; U.S. Pat. No. 5,833,684 Franetzki Nov. 10, 1998, "Handpiece for a stomatological application for laser light"; U.S. Pat. No. 5,825,958 Gollihar, et al. Oct. 20, 1998, "Fiber optic delivery system for infrared lasers"; and U.S. Pat. No. 5,346,489 to Levy et al., "Medical Laser Delivery System." Furthermore, it has been taught that ultraviolet light can be used for the treatment of water. U.S. Pat. No. 5,859,952 Levine, et al. Jan. 12, 1999, "Humidifier with UV anti-contamination provision" and U.S. Pat. No. 5,707,594 to Austin, Jan. 13, 1998, "Pathogen control system" both discuss the use of UV in the treatment of water.

In Levine, a room humidifier has a reservoir for water to be dispersed into the atmosphere, a unit for dispersing the water, and a passage between the reservoir and the unit. The passage is provided with a UV radiation generator for sterilizing water before it reaches the unit. In Austin, a pathogen control system includes at least one germicidal UV tube and at least one UV transmissive tube in proximity thereto. Fluid flow in UV transmissive tube is subjected to ozone produced therein by irradiation by the germicidal UV tube, and fluid flow is controlled with no more than minor attenuation at germicidal UV radiation frequencies.

All of the preceding references are hereby incorporated herein by reference for their teaching.

The present invention utilizes laser-provided light near the "point of use" for the treatment of water generally delivered through waterlines. Although water treatment as taught herein may apply to a wider field of use than the medical field, the specification is most particularly directed to medical instruments, but this direction should not be interpreted in a manner that would narrow the scope of the invention. Treated water delivery to a "point of use" can refer to any uses of water in the medical, environmental, industrial, scientific and commercial industries. The use of uncontaminated water in dental applications, however, is receiving particular attention in the dental profession.

Ultraviolet sterilization is one proven method of eliminating a variety of harmful waterborne microorganisms. Short-wave ultraviolet light (253.7 nanometers) kills waterborne microorganisms with ease, providing they are exposed to the radiation for a sufficient length of time. The UV light breaks the "DNA chain" thus preventing the microorganism from reproducing. All UV sterilizers are a hollow chamber containing an appropriately sized cylindrical UV bulb. Water enters the chamber at the sterilizer inlets, circulates within it for the proper length of time (dwell time) to ensure a high kill rate and returns to the tank via the sterilizer outlet. For maximum benefit, the UV sterilizer must be run on a continuous 24 hour-per-day basis. UV sterilizers are also highly effective at controlling algae blooms in both marine and freshwater aquaria. The portion of the UV light spectrum known to affect living organisms ranges in wavelengths from 190 nm to 400 nm and is divided into 3 bands: UVa, UVb, and UVc. The UVc light band of from 100 nm to 280 nm is often referred to as the germicidal band. UVa and UVb light bands are not useful for water sterilization. Many factors, however, affect the overall effectiveness of UV sterilization: the size of the organism may affect the effectiveness of ultraviolet sterilization (the larger the organism the greater the dosage of UVc light required); UV power (the lamp wattage required for sterilization is related to flow rate of water through the UV sterilizer); contact time (determined by the flow rate of the water through the UV sterilizer, very critical); temperature; and the use of quartz sleeves with UV lamps (the amount of UVc output of the UV lamp dependent on the temperature at which it operates.

After the introduction of the ruby laser in 1960, lasers have become widely used in medicine and dentistry for soft tissue surgical procedures and more specifically the CO2 and Nd:YAG lasers for oral soft tissues surgery. Both of these lasers have FDA approval for this function. In the enhancement of a chemical curettage with a laser, the Nd:YAG is the more ideal because its use of an optical fiber for the transmittal of the laser energy into the gingival sulcus.

The use of laser has proven effective and accurate in medical treatments where, for example, the pulse of light that can vaporize the black pigment of a tattoo but won't affect the red pigment of a spider vein and vice-versa. If used properly, the laser beam won't affect other pigments in the skin, which is what makes lasers so precise and ideal for treating the skin. Lasers also can work to vaporize skin tissue and can be used like a scalpel, to actually cut the skin while at the same time sealing small blood vessels so that the incision is bloodless.

Not all lasers are the same. The difference between them is primarily dependent upon their wavelength. Each laser produces light at a different wavelength with a different intensity in a very specific time period. Wavelength affects both the clinical applications and design of the laser. The wavelength of lasers used in medicine and dentistry generally range from 193 to 348 nanometers to 10,600 nanometers. The Nd:YAG wavelength is in the infrared at 1064 nanometers making this laser light invisible. For this reason a heliumneon laser at 630 nanometers is used in tandem with the devise for aiming purposes.

Lasers designed for surgery deliver concentrated and controllable energy to tissue. For a laser to have a biological effect, the energy must be absorbed. The degree of absorbance in tissue will vary as a function of the wavelength and characteristics of the target. If the peak emission of the laser matches the absorbance spectrum of one or more components of the target tissue, a precise effect will occur. This is extremely important to remember especially in the use of the Nd:YAG for the enhancement of the chemical curettage and more specifically with the incorporation of the sumi ink dye as the black color of the dye is so highly absorbable by the light of the Nd:YAG that the laser has little or no biological effect either on the soft tissues or the hard tissues. The effect is to significantly increase the temperature of the chemical by the laser light being absorbed by the sumi ink.

There are some other characteristics of the Nd:YAG that need to be addressed. The 1064 wavelength will penetrate water to a depth of 60 mm before it is attenuated to 10% of its original strength. This wavelength typically is scattered in soft tissue unless other chromatic enhancements are introduced such as those mentioned above. The heating effect with the Nd:YAG is ideal for ablation of potentially hemorrhagic abnormal tissue, and for control of blood vessels larger that capillary size. Of course this depends greatly on the wattage used and power density at the fiber optic tip. The Nd:YAG is extremely easy to use with its flexible quartz fiber that can penetrate the gingival sulcus similar to a periodontal probe.

There is extensive literature on the effects of the laser on the dental hard tissues with data indicating that changes occur in the enamel and dentin when exposed to laser energy. Because of the varied techniques, nature and extent of these laser studies in relation to their power, wavelength, length of exposure, technique of exposure, and heat created, as well as the effect on the dental pulp, further studies will be necessary to determine their specific effects. Having said this it is important to understand that when using the Nd:YAG for the enhancement of the chemical curettage the primary objective of the Nd:YAG is not to try and alter the dental hard tissue, but to increase the effectiveness of the chemical by increasing its temperature.

The Nd:YAG laser devise that is used for the enhancement of the chemical curettage and root planing is designed and promoted for oral and dental application. It can deliver only up to 3 watts of power in a pulsed mode (20 pulses per second) utilizing a 320 micron quartz fiber. It received FDA clearance for oral soft tissue in 1990. There is abundant evidence confirming markedly less bleeding, particularly of highly vascular oral tissues, with laser surgery. Postoperative pain reduction from oral surgical procedures has been observed after using laser surgery. Delay in the re-epithelization of the sulcular lining of the gingival sulcus has also been noted. These attributes are related to the specific use of the Nd:YAG by itself and therefore may not have the same effects especially with the enhancement of the chemical dye in the gingival curettage.

The technique involved once the chemical has been placed into the gingival sulcus consists of following the usual precautions related to using the Nd:YAG laser. Special safety glasses should be worn by all personal in the operating room as well as the patient. 3 watts of laser power is typically used and pulsed at 20 pps. The 320 micron fiber is inserted into the gingival sulcus parallel to the root surface and is used in an up and down and from side to side motion in the pocketed areas. The black dye of the sumi ink will create a popping sound as the laser light is being absorbed by its color. As this sound diminishes the optical fiber should be advanced to the next pocketed area. Each area should take no longer than five to ten seconds to use up the black chromatic dye.

This laser energy absorbance by the sumi ink increases the temperature of the sodium hypochlorite chemical and enhances its effectiveness. This enhancement is seen in the significant reduction if not elimination of the sulcular microorganisms, the complete removal of the sulcular epithelial lining, and pocket reduction by 1 to 2 mm that is sustained for a period of at least 24 months. This is generally seen as having a significant improvement over the use of root planing and curettage by themselves as well as the possibility of minimizing the scope to periodontal surgery.

Advances in semiconductor lasers (e.g., VCSELS, vertical cavity surface emitting lasers) should also be considered as a source for the delivery of light at the proper wavelength for treatment purposes in accordance with the present invention.

Although the prior teachings of medical lasers are directed to the treatment of body tissue, the laser can also be used effectively to vaporize microorganisms found in water. Referring to FIG. 1, a dental system is illustrated having a water delivery system C-G therein. The apparatuses utilized for delivery of water to the point of use are the handpiece F and/or air/water syringe G. It is at these points in the system that the invention is effective in the treatment of water prior to use for its intended purpose, on a patient.

The typical dental handpiece has a port defined at its end therein where water exits and is directed into a patient's mouth. As shown in FIG. 1, water is supplied through the handpiece via tubing that is connected to the dental station control panel/box. A stream of water may be mobilized generally after the actuation of a switch and/or opening of a manual valving mechanism integrated with the handpiece housing. It is within the tubing, either within the handpiece and/or the distance of tubing between the handpiece and control panel, wherein an increase of microorganisms may far exceed 200 cfu/ml.

Figure 2:
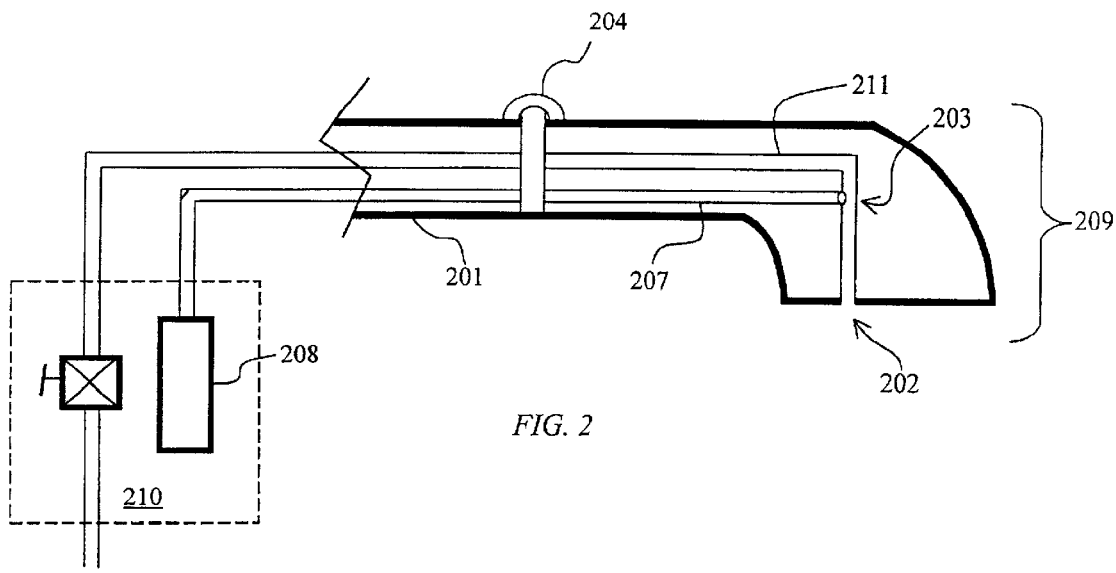
FIG. 2 is a cross-sectional longitudinal view of dental handpiece as used in the prior art.

Referring to FIG. 2, a cross-sectional longitudinal view of dental handpiece 201 in accordance with an embodiment of the present invention is shown. The handpiece 201 can include a fiber optic cable 207 (or waveguide) integrated with the handpiece 201 to provide light from a laser source 208 to a interaction point 203 near the distal end 209 of the handpiece 201 (at a location near the "point of use") and/or on/within the tubing 211, before water is allowed to exit through a port 202 defined at the end of the tubing 211 and handpiece 201 therein and wherefrom water exits and can be directed into a patient's mouth. Water is supplied through the handpiece 201 via tubing 211 because of user interaction with a controller 210 of the dental station and/or on the handpiece 201. The end of the fiber optic cable 210 can be optically integrated with the water tubing 211 at the interaction point 203, thus forming an optical passage similar to a window through which light, selected from a wavelength effective to kill most unwanted microorganisms living within water, is allowed to illuminate and treat water flowing through the tubing 211 at the point of integration 203. When water is allowed to flow through the tubing 211, the laser 208 is also activated causing light to be carried through fiber optic cabling 207 to the head portion 209 of the handpiece near the treatment area 203. Activation of both water and light may be caused by a switching mechanism 204 integrated on the handpiece 201. The switching mechanism 204 may control both water and light functions. Water and light sources may be co-located within a housing 210 typical of most dental stations as shown in FIG. 1. It is generally known by the skilled that a stream of water can be brought on by the actuation of a switch 204 and/or opening of valving within the control panel 210. It is within the tubing 211, either within the handpiece 201 and/or the distance between the handpiece 201 and control panel 210, that the increase of microorganisms generally far exceeds 200 cfu/ml.

Figure 3:
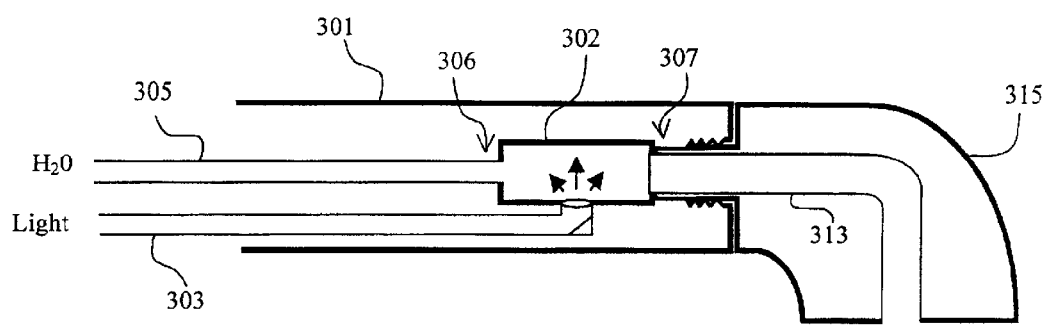
FIG. 3 is a cross-sectional longitudinal view of an embodiment of the invention wherein a dental handpiece having a fiberoptic cable therein provides light from a laser source to a point near the distal end of the handpiece.

Referring to FIG. 3, a cross sectional view of another dental handpiece 301 representing another embodiment of the present invention is shown. A junction box 302 can be employed for water treatment within the handpiece 301. Input tubing 305 carrying water and/or other liquid from the control panel (not shown) to handpiece 301 is connectable to an input portion 306 of a junction box 302. Fiber optic cable 303 can also be connected to/integrated with junction box 302 for delivery of light from the laser light providing source (not shown). Tubing within a head 315 integratable with the handpiece 301 can be connected to an output portion 307 of junction box 302, The head 315 can be removably connectable to handpiece 301 and/or junction box 302, thereby allowing for the dissasembly of the head 315 from handpiece 401 for ease in disinfection/cleaning procedures. Treatment of water will generally take place within the junction box 302. The head 315 can, for example, be screwed onto the handpiece 301 and a rubber gasket (not shown) may be used for creating a seal at an interface point 307 where the tubing 313 interfaces with the junction box 302. Light may be provided/directed into the junction box 302 through the use of lenses, mirrors, fiber and/or optics well known in the art. Water flowing into the treatment area is subjected to light at a wavelength selected for the elimination of microorganisms.

It should be appreciated that the teachings of the present systems and methods for laser water treatment near the point of water's use can be employed in environments broader than the dental industry. Water and/or other liquids may require treatment in other medical fields such as in surgical procedures, environmental fields (e.g., water treatment), industrial (e.g., semiconductor) and other scientific and commercial applications. Referring again to FIG. 3, it should be appreciated that the junction box 302 can be incorporated into other systems. For example, in a water treatment facility, a water line 305 and laser light source 303 can merge into a junction box 301 as a treatment area. After treatment, the water (or other treatable liquid) can be allowed to exit the junction box to its point of use 313, which can include an array of possibilities such as: a water fountain, kitchen sink, and/or equipment rinsing area in an industrial process. It should also be appreciated that although FIGS. 2 and 3 illustrate optical cabling coupled to the treatment areas (i.e., waterline or junction box), it should be appreciated by those skilled in the art that modern semiconductor lasers such as vertical cavity or edge emitting lasers operable at the appropriate wavelength to treat liquids can be optically coupled directly to the treatment areas, or at least be utilized as a source for laser light delivered through optical fiber.

The present invention can also allow for the integration of a laser with other surgical and/or area treatment systems and procedures. It is thus possible to employ a beam directing mechanism to direct laser energy from an exit port and/or the water treatment area within the handpiece to a treatment area within a patient's mouth. Under such a scenario, the beam directing mechanism can be a laser switching or a beam splitter (optical considerations known in the art). A light switch can allow the laser beam to be directed at only one target at a time, whereby a beam splitter allows the beam to strike multiple targets. A light switch can be activated by a microswitch within the handpiece and/or in accordance with control functions at the command of the user. With such an embodiment, water entering a patient's mouth may also be treated with the appropriate wavelength of light from the laser, thus diminishing or reducing harmful microorganisms within the patient's mouth during dental procedures.

The forgoing detailed description of the invention is provided to aid those skilled in the art in practicing the present invention. Even so, the detailed description of the invention should not be construed to unduly limit the present invention, as modifications and variations in the embodiments herein discussed may be made by those of ordinary skill in the art without departing from the spirit or scope of the present invention.

What is claimed is:

1. A water treatment method comprising:
   receiving water into a treatment area;
   introducing light into said treatment area from at least one semiconductor laser as said water passes through said treatment area, wherein microorganisms contained within said water are reactive to said light and are killed; and
   providing said water from said treatment area to a point of use.

2. The method of claim 1 wherein said treatment area is located within a dental handpiece and said point of use is located after a port formed in a head located at the end of said dental handpiece and said treatment area where water exits said dental handpiece and enters a patient's mouth.

3. The method of claim 1 wherein said point of use is after a treatment area located near the head of a dental handpiece.

4. The method of claim 1 wherein said treatment area is a treatment area wherein water and ultraviolet light converge.

5. The method of claim 2 wherein said point of use is located after a head of the dental handpiece.

6. The method of claim 2 wherein said laser beam is controlled by a switching mechanism located on said dental handpiece.

7. The method of claim 1 wherein said treatment area is located at said point of use.

8. The method of claim 1 wherein said treatment area is located within a dental handpiece.

9. The method of claim 1 wherein said treatment area is located with and couple to at least one of a water fountain, a kitchen sink, and/or rinsing equipment in an industrial process.

10. A water treatment system, comprising:
a treatment area further comprising an entry point for receiving water from input tubing connected to the input portion of said treatment area and an exit point for providing water passing through said treatment area to a point of use; and
at least one semiconductor laser coupled to said treatment area for delivery of light into said treatment area;
wherein microorganisms are sensitive to light from said at least one semiconductor laser and are killed as said light penetrates and treats water flowing through said treatment area.

11. The method of claim 10 wherein said treatment area is located with and coupled to at least one of a water fountain, a kitchen sink and/or rinsing equipment in an industrial process.

12. The water treatment system of claim 10 wherein said treatment area is located near a distal end of a dental handpiece.

13. The water treatment system of claim 12 further comprising a head removably connectable to said dental handpiece at said exit point of said treatment area, said head for providing said water to said point of use.

14. The system of claim 13, further comprising a beam directing mechanism for directing light between a light exit port and said treatment area, whereby laser light can also be directed into the an area within a patient's mouth.

15. The system of claim 14 wherein said beam directing mechanism is a laser switching mechanism.

16. The system of claim 14 wherein said beam directing mechanism is a laser splitter.

17. A dental handpiece including a water line for providing water into a treatment area from a port formed in a head associated with the dental handpiece, said dental handpiece comprising:

a laser light source integrated within a dental handpiece housing, said laser light source for providing light from a laser to a water treatment area located near said head of said dental handpiece;

a water treatment area located near said head of said dental handpiece including a entry point for accepting water from a water source into said treatment area, and including an exit point for allowing water to pass from the treatment area toward a point of use through said head.

18. The dental handpiece of claim 17 wherein said treatment area is a junction box integrated within said dental handpiece and coupled to waterline tubing also integrated within said dental handpiece for providing water from a water source into said junction box near said head, wherein water is allowed to exit through said port after treatment by light within said junction box.

19. The dental handpiece of claim 18, wherein said laser light source includes fiber optic cable optically coupled to said junction box, wherein said fiber is coupled such that a window is formed at said junction box through which light is allowed to penetrate and treat water flowing through said treatment area and towards said point of use.

20. The dental handpiece of claim 17 wherein said water treatment area is a location formed by coupling fiber optic cable with waterline tubing near said head, wherein said fiber optic cable is optically integrated with said tubing causing a window through which light is allowed to penetrate and treat water flowing through said waterline tubing at said treatment area, and thereafter said water flows to said point of use.

* * * * *